(12) United States Patent
Lehn et al.

(10) Patent No.: US 8,158,135 B2
(45) Date of Patent: Apr. 17, 2012

(54) IMINE BASED LIQUID CRYSTALS FOR THE CONTROLLED RELEASE OF BIOACTIVE MATERIALS

(75) Inventors: Jean-Marie Lehn, Strasbourg (FR); Nicolas Giuseppone, Strasbourg (FR); Andreas Herrmann, Veyrier (CH)

(73) Assignees: Firmenich SA, Geneva (CH); Universite Louis Pasteur, Strasbourg (FR); Centre National de la Recherche Scientifique, Paris Cedex (FR)

( * ) Notice: Subject to any disclaimer, the term of this patent is extended or adjusted under 35 U.S.C. 154(b) by 737 days.

(21) Appl. No.: 12/294,398

(22) PCT Filed: Mar. 19, 2007

(86) PCT No.: PCT/IB2007/050944
§ 371 (c)(1),
(2), (4) Date: Sep. 24, 2008

(87) PCT Pub. No.: WO2007/113711
PCT Pub. Date: Oct. 11, 2007

(65) Prior Publication Data
US 2009/0306196 A1    Dec. 10, 2009

(30) Foreign Application Priority Data
Mar. 30, 2006  (WO) ............... PCT/IB2006/050961

(51) Int. Cl.
*A61K 9/00* (2006.01)
(52) U.S. Cl. .................................................. 424/400
(58) Field of Classification Search ................ 424/400, 424/84; 514/449, 772, 724, 506, 715, 579; 512/2; 426/650, 237; 392/387
See application file for complete search history.

(56) References Cited

U.S. PATENT DOCUMENTS

| | | | | |
|---|---|---|---|---|
| 3,540,796 A | | 11/1970 | Goldmacher et al. | 350/160 |
| 3,963,638 A | | 6/1976 | Bucher et al. | 252/299 |
| 4,513,034 A | | 4/1985 | Sparer et al. | 428/1 |
| 5,433,857 A | * | 7/1995 | Noble et al. | 210/643 |
| 6,478,440 B1 | * | 11/2002 | Jaworski et al. | 362/96 |

FOREIGN PATENT DOCUMENTS

| | | |
|---|---|---|
| EP | 576 551 B1 | 5/1995 |
| WO | WO 92/16195 | 10/1992 |
| WO | WO 01/68745 A3 | 9/2001 |
| WO | WO 2005/123114 A2 | 12/2005 |

OTHER PUBLICATIONS

Ochsner et al, Status Assessment of Toxic Chemicals: Trichloroethylene, Industrial Environmental Research Laboratory, US EPA, pp. i-x and 1-26 (35 pages total) (1979).*
Material Safety Data Sheet: Trichloroethylene MSDS, Sciencelab. com, Inc., pp. 1-5 (2005).*
Material Safety Data Sheet: Geraniol, Sigma-Aldrich, pp. 1-6 (2011).*
S. Dayagi and Y. Degani, "Reactions of Carbonyl Groups with Amino Groups and Related Reactions" described in: "The chemistry of the Carbon-Nitrogen Double Bond", Ed. Patai, Interscience, NY, pp. 64-83 (1970).
International Search Report PCT/IB2007/050944 Dated Oct. 26, 2007.
H. Kamogawa et al., XP-002084908, *Chemical Release Control—Schiff Bases of Perfume Aldehydes and Aminostyrenes*, Journal of Polymer Science: Polymer Chemistry Ed. vol. 20, (1982), pp. 3121-3129 © 1982 John & Wiley & Sons, Inc.
J.C. Shah et al. *Cubic Phase Gels As Drug Delivery Systems*, Advanced Drug Delivery Reviews 47 (2001), pp. 229-250; © Elsevier Science B.V.
C.C. Müller-Goyman *Physicochemical Characterization of Colloidal Drug Delivery Systems Such as Reverse Micelles, Vesicles, Liquid Crystals and Nanoparticles for Topical Administration* European Journal of Pharmaceutics and Biopharmaceutics 58 (2004), pp. 343-356; © Elsevier B.V.
B.J. Boyd *Controlled Release From Cubic Liquid-Crystalline Particles (Cubosomes)* Surfact. Sci. Ser. (2005), pp. 285-305.

* cited by examiner

*Primary Examiner* — Patricia A Duffy
*Assistant Examiner* — Dennis J Parad
(74) *Attorney, Agent, or Firm* — Winston & Strawn LLP

(57) ABSTRACT

The present invention relates to a delivery system based on a film of an imine forming liquid crystalline phase, mixed with at least with one biologically active substance, to which a constant or variable electric field can be applied. The delivery system can be used as a delivery system for biologically active substances such as flavors, fragrances, bactericides, fungicides, insecticides, insect attractants or repellents, agrochemicals or pharmaceuticals.

14 Claims, 4 Drawing Sheets

Figure 1: Evolution of the isotropic/nematic phase transition temperture ($T_{I/N}$) of N-(4-methoxybenzylidene)-4-butylaniline (MBBA) as a function of increasing amount of different additives in the liquid crystalline phase
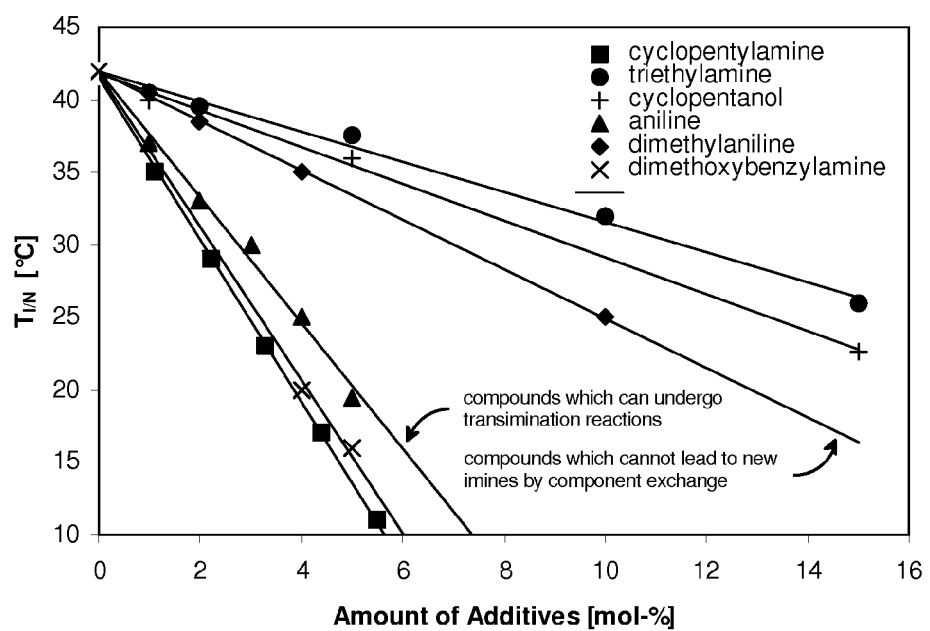

Figure 2: Effect on the strength of the electric field on the constitutional dynamic equilibrium between N-(4-methoxybenzylidene)-4-butylaniline (MBBA) or N-(4-ethoxybenzylidene)-4-butylaniline (EBBA) and cyclopentylamine, respectively, (after 24 h)
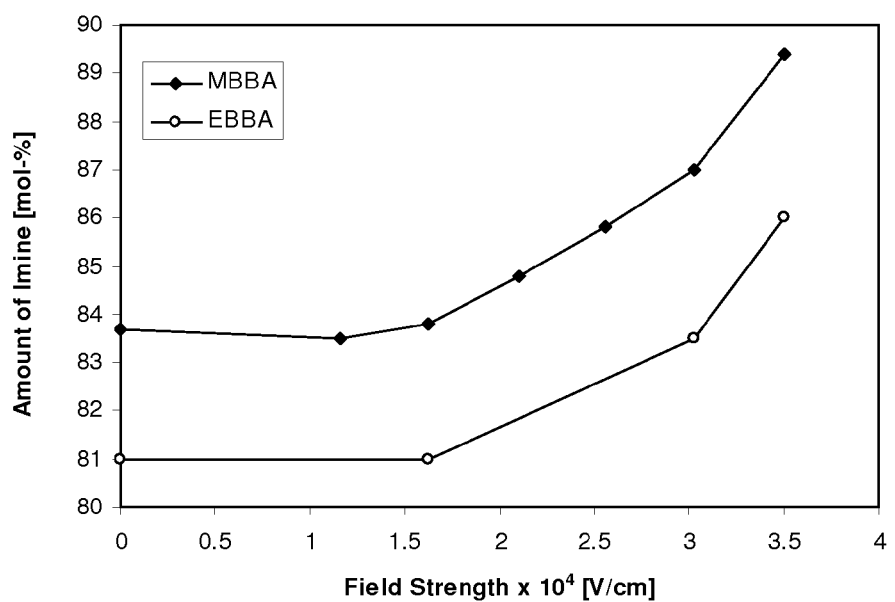

Figure 3: Headspace concentrations measured for the controlled release of cyclopentanol from a mixture with a liquid crystalline phase forming imine (N-(4-methoxybenzylidene)-4-butylaniline) in dependence on the applied voltage
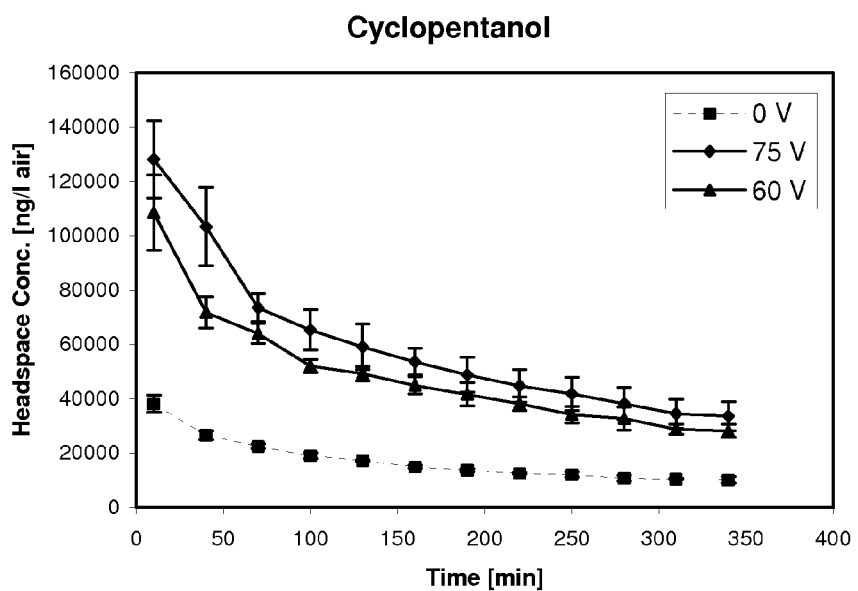

Figure 4: Headspace concentrations measured for the controlled release of benzaldehyde (■), 4-ethylbenzaldehyde (●), 4-methoxybenzaldehyde (▲) and acetophenone (x) from a mixture with a liquid crystalline phase forming imine (N-(4-methoxybenzylidene)-4-butylaniline) in the presence (solid lines) or absence (dotted lines) of an electric field
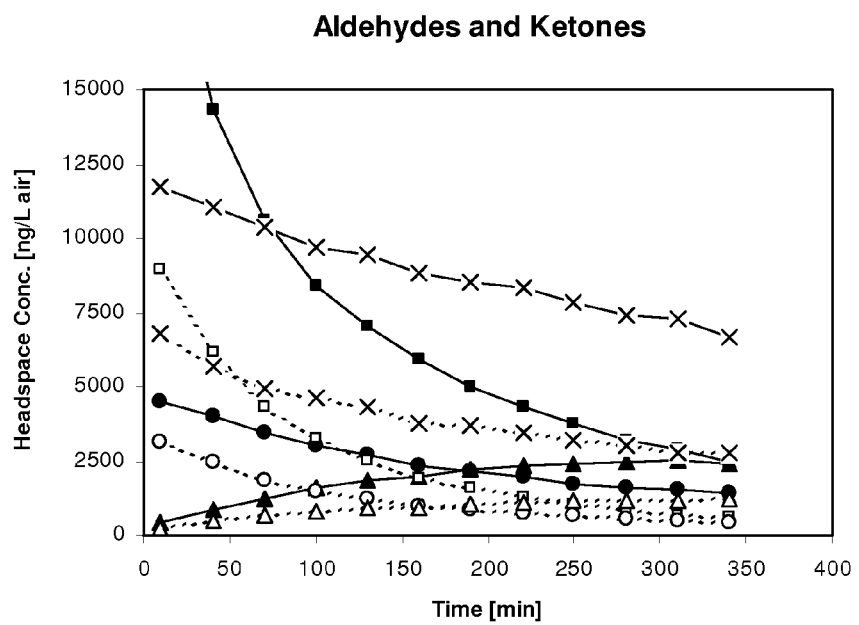

IMINE BASED LIQUID CRYSTALS FOR THE CONTROLLED RELEASE OF BIOACTIVE MATERIALS

This application is a 371 filing of International Patent Application PCT/IB2007/050944 filed Mar. 19, 2007 and claims the benefit of International Application PCT/IB2006/050961 filed Mar. 30, 2006.

TECHNICAL FIELD

The present invention relates to the field of perfume delivery and in particular to a delivery system based on a liquid crystalline phase obtained from imines. Said delivery system can release in a controlled manner a biologically active volatile material at rates which can be controlled by applying a variable electric field to the system. The invention concerns also the use of the delivery system as well as the consumer articles comprising said delivery system.

PRIOR ART

For optimal performance biologically active compounds such as flavors, fragrances, bactericides, fungicides, insecticides, insect attractants or repellents, agrochemicals or pharmaceuticals have to be delivered at the right moment and at a well defined rate. The search for efficient delivery systems for bioactive materials is therefore an important field of activity in various domains of research in different types of industries. Especially the development of stimuli responsive delivery systems and devices have attracted much attention during the last couple of years. Numerous delivery systems obtained either by encapsulating the active substance into a suitable matrix or capsule or by chemical conjugation to a suitable substrate have been reported. Materials responding to external triggers such as enzymes, water (pH), light, oxygen or temperature have been prepared and used in various practical applications. Due to their polarity and/or chemical nature, only a restricted selection of active materials can be successfully released from individual capsules or conjugates, respectively. Electric triggers are generally less sensitive towards the polarity and chemical functionality of bioactive molecules and are therefore interesting to release a broad variety of compounds from a suitably designed device.

Liquid crystals, which are employed in display technology, optical data storage or non-linear optics, are very well-organized systems. They can exist in various phases depending on the constitution of the mixtures and the molecular structures of the liquid crystalline phase forming compound involved. They found use as particles, gels, capsules or waxes for the encapsulation of active substances into the (lamellar or cubic) liquid crystalline phase. Liquid crystalline systems, mainly in a polymeric form, were used in pharmaceutical applications for the slow release of drugs (see for example: J. C. Shah et al., Adv. Drug. Delivery Rev., 2001, 47, 229-250, C. C. Müller-Goymann, Eur. J. Pharm. Biopharm., 2004, 58, 343-356 or B. J. Boyd, Surfact. Sci. Ser., 2005, 127, 285-305), and also for the release of flavors and fragrances in foods or cosmetics (see for example: EP 0 576 551). The release of the active substance from liquid crystalline delivery systems is often controlled by diffusion, and some systems using the photoinduced or thermal phase transition of the liquid crystals as the release triggers have been reported (see for example: WO 01/68745). Besides delivery systems which release compounds slowly over time, there is interest in the development of delivery systems that can rapidly release active substances upon an external trigger thus allowing their use as olfactive stimuly-response materials in air-freshening or insect attractant or repellent devices. A rapid response to the external trigger is thus a prerequisite for a well-performing delivery system of this type. The use of electric fields to release molecules by inducing a phase change of polymeric liquid crystalline compounds, namely polypeptides, has for example been disclosed in U.S. Pat. No. 4,513,034 or WO 2005/123114. However, to the best of our knowledge, none of the prior art documents suggests, or allows to expect, that imines capable of forming non-polymeric liquid crystalline phase are, dependent on the strength of the electric field that is applied, suitable as delivery systems for the rapid stimuly-responsive release of (volatile) bioactive substances which are either not participating in nematic phase formation or which are generated by component exchange with the liquid crystalline phase forming imines.

DESCRIPTION OF THE INVENTION

We have now surprisingly found that, upon application of an electric field, imines with a negative dielectric anisotropy capable of forming liquid crystalline phases tend to release molecules that do not participate in the formation of nematic phases and that the electric field has a direct effect on the thermodynamic equilibria and kinetics. These phenomena are useful for the design of delivery systems for the controlled release of biologically active volatile material.

Indeed, dependent on the strength of the electric field that is applied, the biologically active volatile material, which is not participating in nematic phase formation, gets released. The rate of release of the active substances is dependent on the strength of the electric field, as well as on the diffusion of said substances out of the electric device.

The present invention relates to the use of a delivery system, composed of a mixture of at least one imine capable of forming a liquid crystalline phase and at least one biologically active volatile material, to release in a controlled manner said biologically active volatile material, in which method the release of said the volatile material can be improved upon application of an electric field to said mixture. Another aspect of the present invention are the delivery systems.

By "imine capable of forming a liquid crystalline phase" it is meant an imine derivative which can undergo a liquid crystalline phase change as a response to an external trigger, such as for example an electric field.

Therefore, a first aspect of the present invention is a method for releasing in a controlled manner, into the surrounding space, a biologically active volatile material which method comprises the application of a variable electric field to a delivery system comprising:

1) at least one imine capable of forming a liquid crystalline phase and being of formula (I)

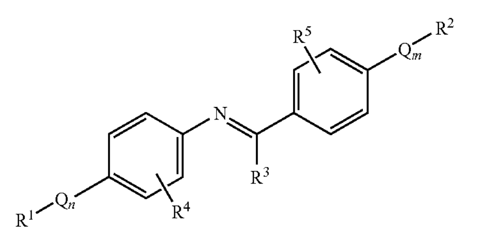

wherein $R^1$ and $R^2$ represent independently of each other a $C_1$-$C_{18}$ linear, branched or cyclic alkyl, alkenyl or alkoxy chain or a substituent selected from group consisting of CN, OCOX, OCOC$_6$H$_5$X, C$_6$H$_5$X, COX, COOH, H, Cl, Br, I, NO$_2$, OH, CF$_3$, N(CH$_3$)$_2$, X being CF$_3$ or a C$_1$-C$_{18}$ linear or branched alkyl or alkenyl chain; and R$^3$ is H or a linear or branched C$_1$-C$_8$ alkyl or alkenyl chain;

n and m are 0 or 1, and with the proviso that n=m=1 is excluded; and

Q is selected from the group consisting of formulae i) to v),

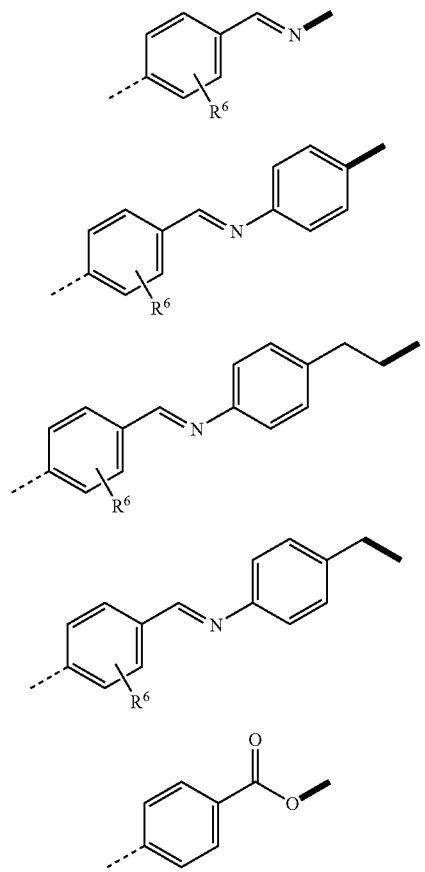

in which formulae if n=1 the dotted lines of formula i) to v) indicate the connection to R$^1$ and the bold lines the connection to the aromatic ring of formula (I), if m=1 the dotted lines indicate the connection to the aromatic ring and the bold lines the connection to R$^2$;

R$^4$, R$^5$ and R$^6$ are, independently from each others, selected from the group consisting of H, Cl, OH, OCH$_3$, CH$_3$, CN, NO$_2$, N(CH$_3$)$_2$; or R$^1$ and R$^4$, and/or R$^2$ and R$^5$, and/or R$^1$ and R$^6$, and/or R$^2$ and R$^6$ taken together, respectively, form a 5 or 6 membered ring containing 2 oxygen atoms; and with the proviso that at least one of the groups of R$^1$ or R$^2$ represents a C$_1$-C$_{18}$ linear or branched alkyl, alkenyl or alkoxy chain;

2) at least one biologically active volatile material in the form of a C$_5$-C$_{30}$ volatile perfuming, flavoring, pharmaceutical, insect repellent or attractant, insecticide, antibacterial, fungicide or agrochemical ingredient.

As will be showed further below, and in particular in the examples, said method presents several advantages, namely can be obtained an improved release, said release can be obtained very quickly and can be modulated by choosing the intensity of the electric field.

For the sake of clarity, and from what is described above or below, it is self evident that the expression "application of a variable electric field" implies that the electric field can be varied as desired in order to achieve the desired speed of release.

According to another particular embodiment of the invention, the preferred imine (I) is a compound wherein:

R$^1$ and R$^2$ represent independently of each other a C$_1$-C$_{18}$ linear or branched alkyl, alkenyl or alkoxy chain or a substituent selected from group consisting of CN, OCOX, OCOC$_6$H$_5$X, C$_6$H$_5$X, COX, COOH, Cl, Br, I, NO$_2$, OH, CF$_3$, N(CH$_3$)$_2$, X being a C$_1$-C$_{18}$ linear or branched alkyl or alkenyl chain;

R$^3$ is H or a linear or branched C$_1$-C$_8$ alkyl or alkenyl chain;

n and m are 0 or 1, and with the proviso that n=m=1 is excluded; and

Q is selected from the group consisting of formulae i) or ii); and

R$^4$ and R$^5$ are, independently from each other, selected from the group consisting of H, Cl, OH, OCH$_3$, CH$_3$; or R$^1$ and R$^4$, and/or R$^2$ and R$^5$ taken together, respectively, may form a 5 or 6 member ring containing 2 oxygen atoms; and with the proviso that at least one of the groups of R$^1$ or R$^2$ represents a C$_1$-C$_{18}$ linear or branched alkyl, alkenyl or alkoxy chain.

Alternatively, according to a further embodiment of the present invention the imine (I) is a compound of formula

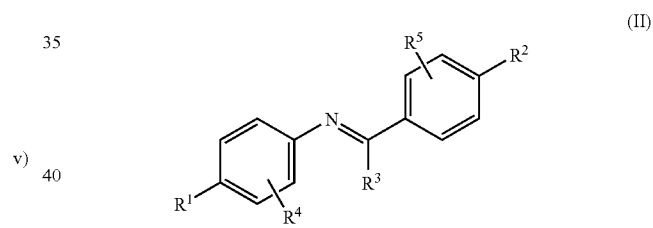

(II)

wherein R$^1$ and R$^2$ represent independently of each other a C$_1$-C$_{18}$ linear alkyl, alkenyl or alkoxy chain or a substituent selected from group consisting of CN, OCOX, OCOC$_6$H$_5$X, C$_6$H$_5$X, COX, COOH, OH, X being CH$_3$, CH$_2$CH$_3$, CH(CH$_3$)$_2$, or C(CH$_3$)$_3$;

R$^3$ is H or a linear or branched C$_1$-C$_4$ alkyl chain; and

R$^4$ and R$^5$ are H, OH, OCH$_3$; or R$^1$ and R$^4$, and/or R$^2$ and R$^5$ taken together, respectively, may form a 5 or 6 member ring containing 2 oxygen atoms; and with the proviso that at least one of the groups of R$^1$ or R$^2$ represents a C$_1$-C$_{18}$ linear alkyl, alkenyl or alkoxy chain.

Preferred compounds of formula (I) are those wherein R$^3$ is H.

More preferred compounds of formula (II) are those wherein R$^1$ and R$^2$ represent independently of each other a C$_1$-C$_{18}$ linear alkyl or alkoxy chain;

R$^3$, R$^4$ and R$^5$ are a hydrogen atom; or R$^1$ and R$^4$, and/or R$^2$ and R$^5$ taken together, respectively, may form a 5 or 6 member ring containing 2 oxygen atoms; and with the proviso that at least one of the groups of R$^1$ or R$^2$ represents a C$_1$-C$_{18}$ linear alkyl, alkenyl or alkoxy chain.

Furthermore, according to any of the embodiments mentioned above, preferred compounds of formula (I)/(II) are imines with a negative dielectric anisotropy.

Compounds of formula (I) described above are commercially available or can be synthesized by condensation of amines with carbonyl derivatives (i.e. the compounds of formula (III) or (IV)) as described in the literature (see for example: S. Dagay and Y. Degani in "The Chemistry of the Carbon-Nitrogen Double Bond", Ed. Patai, Interscience, New York, 1970, p. 64-83) or in standard textbooks of organic chemistry.

Said biologically active volatile material can be aldehydes, ketones, alcohols, amines, esters, ethers, lactones or nitriles, which are entrapped within the liquid crystalline phase and released to the surroundings upon application of an electric field. As mentioned above, said biologically active volatile material can be an ingredient capable of bringing a benefit or effect into its surrounding environment, and having, in particular, a perfuming, flavoring, pharmaceutical, insect repellent or attractant, insecticide, fungicide, antibacterial, agrochemical effect and mixtures thereof. By "volatile" it is meant a compound having a molecular weight ideally comprised between 80 and 250 g/mol and/or a vapor pressure above 0.05 Pa at standard conditions.

BRIEF DESCRIPTION OF THE DRAWINGS

FIG. 1 shows the evolution of the isotropic/nematic phase transition temperture ($T_{IN}$) of N-(4-methoxybenzylidene)-4-butylaniline (MBBA) as a function of increasing amount of different additives in the liquid crystalline phase.

FIG. 2 shows the effect on the strength of the electric field on the constitutional dynamic equilibrium between N-(4-methoxybenzylidene)-4-butylaniline (MBBA) or N-(4-methoxybenzylidene)-4-butylaniline (EBBA) and cyclopentylamine, respectively, (after 24 h).

FIG. 3 shows the headspace concentrations measured for the controlled release of cyclopentanol from a mixture with a liquid crystalline phase forming imine (N-(4-methoxybenzylidene)-4-butylaniline) in dependence on the applied voltage.

FIG. 4 shows the headspace concentrations measured for the controlled release of benzaldehyde (■), 4-ethylbenzaldehyde (●), 4-methoxybenzaldehyde (▲) and acetophenone (×) from a mixture with a liquid crystalline phase forming imine (N-(4-methoxybenzylidene)-4-butylaniline) in the presence (solid lines) or absence (dotted lines) of an electric field.

DETAILED DESCRIPTION OF THE PREFERRED EMBODIMENTS

In a preferred embodiment of the present invention, the biologically active volatile material is a perfuming ingredient, a flavoring ingredient, or an insect repellent or attractant.

Furthermore, said biologically active volatile material can be a $C_5$-$C_{30}$ aliphatic or aromatic hydrocarbon, aldehyde, ketone, carboxylic ester, ether, lactone, nitrile, ether, amine, or alcohol derivatives, as well as mixtures thereof. Preferably, said biologically active volatile material is a $C_5$-$C_{15}$ alcohol, ester, ether, lactone, nitrile, aldehyde or ketone.

According to any one of the above embodiments, the delivery system comprises a compound of formula (I) as defined in claim 1, and at least one $C_5$-$C_{15}$ volatile perfuming, flavoring, pharmaceutical, insect repellent or attractant, insecticide, antibacterial, fungicide or agrochemical ingredient, said ingredient being an alcohol, ester, ether, lactone, nitrile.

Furthermore, when the biologically active volatile material is a perfuming ingredient, said active material is preferentially enough volatile to be perceived and can therefore be characterized by a vapor pressure above 2.0 Pa, as obtained by calculation using the software EPIwin v 3.10 (available at 2000 US Environmental Protection Agency). According to another embodiment said vapor pressure is above 5.0, or even above 7.0 Pa.

By "perfuming ingredient" it is meant here a compound, which is used in perfuming preparation or composition to impart a hedonic effect. In other words such ingredient, to be considered as being a perfuming one, must be recognized by a person skilled in the art as being able to impart or modify in a positive or pleasant way the odor of a composition, and not just as having an odor. Examples of such ingredients can be found in reference texts such as the book by S. Arctander, Perfume and Flavor Chemicals, 1969, Montclair, N.J., USA, or its more recent versions, or in other works of a similar nature, as well as in the abundant patent literature in the field of perfumery.

A person skilled in the art will be perfectly able to choose the ingredients, as well as their concentrations, needed for the manufacture of an active substance imparting the desired benefits and, at the same time, allowing the composition of the invention's delivery system.

By "insect attractant or repellent" it is meant a compound having a positive or negative effect on insects. Examples of such ingredients can be found in reference texts or in other works of a similar nature as for example: A. M. El-Sayed, The Pherobase 2005, http://www.pherobase.net.

The concentration of the biologically active volatile material, in the delivery system can be varied between 1 and 50 mol %, preferably between 5 and 30 mol %, more preferably between 10 and 25 mol %, in respect to the amount of imine (I).

According to a particular embodiment of the invention, when the biologically active volatile material is an aldehyde, ketone or amine, then the invention also includes a delivery system obtainable by admixing
i) at least one aldehyde or ketone of general formula:

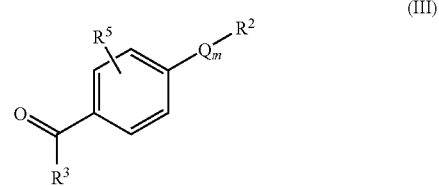

(III)

ii) at least one amine of general formula

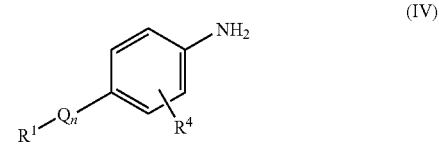

(IV)

wherein $R^1$, $R^2$, $R^3$, $R^4$, $R^5$, Q, n and m have the same meaning as indicated above; and
iii) at least one biologically active volatile aldehyde, ketone or amine.

Preferred compounds of formula (III) are those wherein $R^3$ is H.

The resulting delivery system will comprise at least an imine of formula (I), the free biologically active volatile material, as well as other imines obtained by the interaction of compounds (III)/(IV) with part of the biologically active volatile aldehyde, ketone or amine.

In said delivery system the aldehyde or ketone (III) and the amine (IV) are preferably admixed in equimolar amounts, while the biologically active volatile aldehyde, ketone or amine in amounts similar to those described above for the biologically active volatile material. Preferably the compounds (III) and (IV) have a volatility lower than those of the biologically active volatile aldehyde, ketone or amine.

As anticipated above, the delivery systems described above are also an object of the present invention.

Without being bonded by the theory, in this embodiment of the invention, it is believed that the biologically active volatile aldehyde or amine is partitioned into two sets. The first set comprises substances which cannot form covalently bonded adducts with the amines and which are not participating in the liquid crystalline phase formation. The second set comprises active amines, aldehydes or ketones that may form covalent bonds with the amines, i.e. undergo constitutional reorganization with the amine to form an imine. Said second set is capable to undergo component exchange and to be released with different kinetics, as shown in Scheme 1.

Scheme 1: Constitutional reorganization by component exchange in the presence of an electric field.

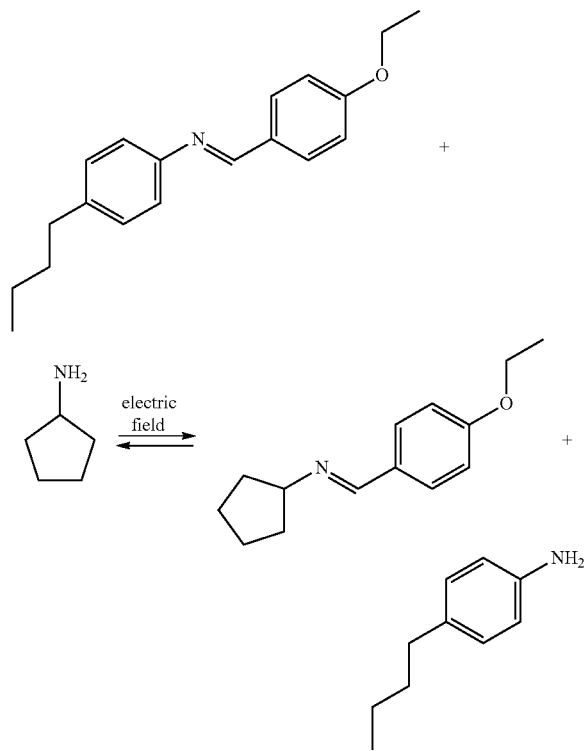

Therefore, it is believed that the biologically active volatile material can be trapped in the matrix of the delivery system by covalent bonding to some of its constituents and by physical entrapment into the liquid crystalline phase or only by physical entrapment.

The presently described delivery system may further contain small amounts of salts, preferably organic salts which are at least partly soluble in the liquid crystalline phase. These salts can be composed of a metal or an ammonium cation and an organic carboxylate, sulfonate, benzoate or benzenesulfonate anion. Some typical examples for suitable salts that may be used are described in U.S. Pat. No. 3,963,638. The salts are added in small amounts ranging from $10^{-3}$ to $10^{-7}$ moles per average mole of imine capable of forming a liquid crystalline phase. Preferably the salt concentration varies between $10^{-4}$ to $10^{-7}$ moles with respect to the molar amount of said imine.

Another object of the invention is a device (or element) for releasing or dispensing in a controlled manner, in the surrounding space, a biologically active volatile material.

Said device comprises:

i) the above-described delivery system;

ii) an apparatus allowing the application of an electric field to said delivery system, and said apparatus being in contact with said delivery system; and iii) optionally, a means to apply an electric field, or a voltage, connected to said apparatus.

According to a particular embodiment of the invention, a second kind of device can be described as comprising:

i) the above-described delivery system;

ii) an apparatus allowing the application of an electric field to said delivery system, and being in the form of a container, containing said delivery system; and iii) optionally, a means to apply an electric field, or a voltage, connected to said container.

Preferably said container or apparatus is composed of a non-conducting material and possesses at least two distinct sections made of a conducting material and to which said means to apply an electric field, or a voltage, can be connected. Furthermore said container or apparatus can be sealed using a film made of a material permeable to the volatile biologically active volatile materials.

According to a particular embodiment of the invention, a third kind of device can be described as comprising:

a film of the above-described delivery system;

two conducting surfaces to which a constant or variable electric field can be applied, and between which is inserted said film, and which are in contact with said film; and optionally, a means to apply an electric field, or a voltage, connected to said solid surface.

As mentioned, the conducting surfaces are in direct contact with the delivery system. Said surface can be made of a conducting material such as a metal, a metal oxide or a mixture thereof, or can be composed of a non-conducting material, e.g. made of glass or ceramics, having a surface coated with a conducting material, the latter being in contact with the delivery system.

The two conducting surfaces have preferentially a similar form and may, for example, have a continuous surface or a surface including several holes so as to allow for a better evaporation of the active material to be released.

The film thickness of the liquid crystalline phase containing the active substances may influence the speed of release of the active substances. The film thickness between the two conducting surfaces can vary between 1 and 2000 μm, preferably between 10 and 500 μm or even more preferably between 10 and 150 μm.

In other words the device can be in the form of a sandwich of various layers, such as for example (non-conducting material)-(conducting material)-delivery system-(conducting material)-(non-conducting material), the means to apply the voltage being connected with the conducting material.

According to an embodiment of the invention, the means to apply an electric field can be an electric circuit which can be powered by either batteries or a power supply.

The voltage applied to the liquid crystalline phase can vary between 0.0 and 230 V, preferably between 0.0 and 100 V, and even more preferably between 0.0 and 80V. When said voltage is set at 0.0 V the delivery is minimal. Of course depending on the desired type of device and rate of release, the skilled person can envisage devices wherein the voltage is at minimum 0.1 V or even 1.0 or 5.0 V.

The strength of the electric field depends on the thickness of the film and on the voltage applied to it. According to an embodiment of the invention, the electric field strength is preferably selected to be lower than $1 \times 10^5$ V/cm, even more preferably lower than $5 \times 10^4$ V/cm.

The device of the invention is particularly suitable for the manufacture of a consumer article for dispensing a volatile material in the surrounding space. Thus, a consumer article containing, or associated with, at least one device according to the invention is also an object of the present invention. When at least one of the devices of the invention's consumer article comprises a perfuming ingredient, than said consumer article can be in the form of an air freshener, a car freshener, a closet freshener, a cat litter box freshener, a shoe freshener or a garbage pail freshener. When at least one of the devices of the invention's consumer article comprises an insect attractant or repellent ingredient, than said consumer article can be an insecticide or an insect attractant or repellent article.

The consumer article of the invention can be operated with batteries or suitably transformed electric current from the power supply. In the case that more than one device is present, said devices can be in parallel or in series, and it is also understood that the composition of each the delivery system comprised in each device can be different from each others. Alternatively each device can be operated separately from each other.

The consumer article according to the invention can be combined with a mechanical, electrical or optical switch that allows to generate the electric field either manually or automatically, as well as in combination with other devices generating an electric signal, such as a rheostat. Of particular interest is the combination of the device with light switches, ventilators, time-lag relays, time switches or combinations thereof. The delivery system of the invention may have any suitable shape.

It is also understood that the consumer article may also be built into a suitable container. In such a case, different types of containers can be used. As non limiting examples, one can cite a container made of a material totally impermeable to the vapors of the volatile liquid component and which possesses at least an aperture through which the vapors of the volatile liquid component can be diffused into the air surrounding said consumer article. Alternatively, the container can envelope entirely the device and at least a portion of said container allows the escape of the vapors (permeable) of the volatile liquid component into the air surrounding said consumer article (e.g. said portion is made of a material which allows the escape of the vapors or comprises one or a plurality of holes).

Whatever or not the consumer article includes a container, in order to prevent diffusion of vapors of the volatile liquid into the surroundings during storage, said consumer article, or the portion of the container which is permeable to the volatile liquid's vapors, can be sealed by any known means, such as a plastic film, which is impermeable to the volatile liquid phase vapors. The consumer will then activate the consumer article simply by removing the sealing and/or plugging/switching on the device or devices, after which the volatile liquid phase will start to diffuse into the surrounding air.

EXAMPLES

The invention will now be described in further detail by way of the following examples, wherein the abbreviations have the usual meaning in the art. NMR spectral data were recorded in $CDCl_3$ on a Bruker Avance 400 MHz spectrometer at 400 MHz for $^1H$ and at 100.6 MHz for $^{13}C$, or on a Bruker AV 500 spectrometer at 500 MHz for $^1H$ and at 125.8 MHz for $^{13}C$, the chemical displacements δ are indicated in ppm with respect to TMS as the standard, the coupling constants J are expressed in Hz. Electric fields were generated with a Thurlby Thandar Instruments TTi EX752 M multi-mode power supply between two indium tin oxide (ITO) coated glass slides (origin: Aldrich, 70-100 ohm resistance, ca. 7.0×2.5 cm). Film resistivities were measured with a Keithly 6517A instrument. UV/Vis spectra were recorded on a Varian Cary 3 instrument. GC/MS (EI) spectra were recorded on an Agilent 6890N GC system equipped with a capillary column (DB-1, 30 m, 0.25 mm i.D.) coupled with an Agilent MSD 5973N quadrupole mass spectrometer (electron energy ca. 70 eV).

Example 1

Influence of the Amount of Different Additives on the Phase Transition Temperature of Liquid Crystalline Phase Forming Imines Isotropic/nematic phase transition temperatures ($T_{I/N}$) were measured by variable temperature UV/Vis spectroscopy in the presence of variable amounts of different additives. In a typical experiment, 200 μL of N-(4-methoxybenzylidene)-4-butylaniline (MBBA) containing varying amounts of cyclopentanol, triethylamine, dimethylaniline, aniline, cyclopentylamine or dimethoxybenzylamine, respectively, were placed inside a UV microcell to give a film thickness of ca. 10 μm. The UV/Vis absorption of the film was measured between 18° C. and 60° C. at 400 nm using 1° C./min heating/cooling cycles.

The following data were obtained:

| | $T_{I/N}$ [° C.] of MBBA in the presence of different additives | | | | | |
| --- | --- | --- | --- | --- | --- | --- |
| Amount [mol-%] | cyclo-pentanol | triethyl-amine | dimethyl-aniline | aniline | cyclopentylamine | dimethoxy-benzylamine |
| 0 | 42 | 42 | 42 | 42 | 42 | 42 |
| 1 | 40 | 40.5 | 40.5 | 37 | — | — |
| 1.1 | — | — | — | — | 35 | — |

-continued

T$_{I/N}$ [° C.] of MBBA in the presence of different additives

| Amount [mol-%] | cyclo-pentanol | triethyl-amine | dimethyl-aniline | aniline | cyclopentylamine | dimethoxy-benzylamine |
|---|---|---|---|---|---|---|
| 2 | — | 39.5 | 38.5 | 33 | — | — |
| 2.2 | — | — | — | — | 29 | — |
| 3 | — | — | — | 30 | — | — |
| 3.3 | — | — | — | — | 23 | — |
| 4 | — | — | 35 | 25 | — | 20 |
| 4.4 | — | — | — | — | 17 | — |
| 5 | 36 | 37.5 | — | 19.5 | — | 16 |
| 5.5 | — | — | — | — | 11 | — |
| 10 | — | 32 | 25 | | — | |
| 15 | 22.6 | 26 | | | — | |

The data illustrated in FIG. 1 show that the phase transition temperature T$_{I/N}$ decreases linearly with increasing amount of compounds added to the liquid crystalline phase forming imine. Two sets of added compounds can be distinguished. The first set comprises compounds which cannot lead to a new imine by component exchange and where addition of about 15 mol-% results in a decrease of T$_{I/N}$ of the imine to room temperature. The second set contains compounds that can react with the imine by transimination reactions and where the addition of only 3 mol-% decreases the T$_{I/N}$ to room temperature.

Example 2

Release of Compounds by Component Exchange from a Mixture of Constitutionally Interrelated Compounds in the Presence of an Electric Field Liquid crystalline phase forming N-(4-methoxybenzylidene)-4-butylaniline (MBBA, 200 µL) was mixed with cyclopentylamine (15.2 µL) in a closed vial. The mixture was then heated up to 60° C. for 5 minutes, cooled down to room temperature and left for 2 hours. Then 38 µL (±5%) of the neat mixture were placed between the metal coated sides of two ITO slides using a microsyringe. The glass slides were gently pressed together in order to get a thin film covering the surface (ca. 18.1 cm$^2$). The film thickness was ca. 21 µm (±5%). The slides were then thermostatted at 22.5° C., and the slide connected to the cathode and anode of the power supply, respectively. The temperature was regulated by placing the ITO slides on a thermostatted surface, controlled by a Polystat cc2 Huber system. The temperature was measured at the surface of the glass slides with a Bead Probe Keithly 6517-TP thermocouple. The electric field was applied by varying the voltage of the generator between 0 and 75 V (for an applied field of 75 V, the experimental errors will lead to a value of 3.5×10$^4$ V/cm (±0.15×10$^4$ V/cm). The maximum field applied was 3.5×10$^4$ V/cm in order to keep a high resistivity (≧6.0×10$^7$ Ω/cm) to avoid fast degradation of the compounds and heating phenomena. After a given time, the electric field was shut off, and the film between the slides was dissolved in CDCl$_3$ (2 mL), immediately before $^1$H NMR measurements (within 5 minutes). To avoid the catalysis of the transimination reaction, traces of acid contained in the CDCl$_3$ were removed immediately prior to use by flash chromatography through neutral alumina. $^1$H NMR spectra were recorded until stabilization of the equilibria for both, the experiment with the applied electric field and the control experiment without electric field, which was carried out under the same conditions.

The same experiment was carried out with a mixture of liquid crystalline phase forming N-(4-ethoxybenzylidene)-4-butylaniline (EBBA, 200 mg), which was recrystallized by slow cooling of a hot saturated solution in heptane, and cyclopentylamine (15.2 µL).

The following data were obtained (see FIG. 2):

| Field Strength × 10$^4$ [V/cm] | Quantity of MBBA [mol-%] | Quantity of EBBA [mol-%] |
|---|---|---|
| 0 | 83.7 | 81.0 |
| 1.16 | 83.5 | |
| 1.63 | 83.8 | 81.0 |
| 2.10 | 84.8 | |
| 2.56 | 85.8 | |
| 3.03 | 87.0 | 83.5 |
| 3.50 | 89.4 | 86.0 |

The fact that the exchange compounds N-(4-methoxybenzylidene)cyclopentylamine and N-(4-ethoxybenzylidene)cyclopentylamine do not form liquid crystalline phases results in a change of the isotropic/nematic phase transition temperatures T$_{I/N}$. Due to the opacity of the nematic phase under a high electric field, the phase transition could be observed with the naked eye and with a polarized light microscope.

Several other mixtures using aniline, benzylamine, isopentylamine, allylamine and even libraries containing all these amines led to similar observations. In all these cases the volatile amines were released by evaporation.

To prove that the equilibration of the transimination reaction depends on the electric field and not on the evaporation of the added compound, an electric field was applied to a film of a mixture of N-(4-ethoxybenzylidene)cyclopentylamine and 2-methoxyaniline (in a molar ration of 79.3:20.7). With a melting point of 225° C., 2-methoxyaniline has a relatively low volatility. The relative variation of the percentage of 4-butylaniline, which is formed by component exchange, was followed by $^1$H NMR spectroscopy after 2 h of equilibration at 24° C. as described above. The spectra showed an increase in the amount of N-(4-ethoxybenzylidene)cyclopentylamine and 2-methoxyaniline at equilibrium and a decrease of 4-butylaniline and (4-ethoxybenzylidene)-(2-methoxyphenyl) amine when the electric field was applied. The increase of 2-methoxyaniline in the mixture shows that compound evaporation cannot be the driving force for the component exchange. Furthermore, the electric field induced perturbation of the system was found to be fully reversible. A temperature induced phase transition resulted in only minor changes in the composition of the sample and could thus be ruled out.

Example 3

Headspace Analysis for the Release of Substances that can not Form New Imines by Constitutional Reorganization in the Presence of an Electric Field Cyclopentanol (20 μL) was mixed with N-(4-methoxybenzylidene)-4-butylaniline (200 μL). Then 100 μL of the solution were placed with a Socorex-pipette onto the coated side of an ITO slide and covered with a second slide in that way that the coated side is in contact with the solution. To keep a constant distance between the two slides a teflon film (GEB, Olifan P.T.F.E., thickness 0.1 mm) was cut to give two stripes being ca. 6 mm large, which were placed at both ends between the two ITO glass plates. The slides were pressed together to form a uniform and transparent film covering almost the complete surface between the slides. The two ITO slides then were taped onto a glass support and the ends of each slide connected to the cathode and anode of the power supply, respectively. The glass slides were placed inside a homemade headspace sampling cell (average volume ca. 625 ml) with the cables to the power supply passing through a teflon stopper at the top of the cell, allowing a gas tight fixing of the cables to the power supply. A constant air flow of ca. 205 ml/min was aspirated through an active charcoal filter, a saturated solution of NaCl (to ensure a constant humidity of the air) and the headspace sampling cell and the volatiles evaporated from the system trapped on a Tenax® cartridge. The measurement was started by switching on the pump and, after 1 min, the voltage of the power supply. During 10 min the headspace system was left equilibrating while sampling on a waste Tenax® cartridge, then the volatiles were adsorbed during 1 min on a clean Tenax® cartridge. The sampling was repeated 11 times every 29 min. The cartridges were desorbed on a Perkin Elmer TurboMatrix ATD desorber coupled to a Carlo Erba MFC 500 gas chromatograph equipped with a J&W Scientific DB1 capillary column (30 m, i.d. 0.45 mm, film 0.42 μm) and a FID detector. The volatiles were analyzed using a two step temperature gradient starting from 70° C. to 130° C. at 3° C./min and then going to 260° C. at 25° C./min. The injection temperature was at 240° C., the detector temperature at 260° C. The experiments were carried out in triplicate by applying a voltage of 75 V, 60 V or 0 V (reference), respectively. Headspace concentrations (in ng/L) were obtained by external standard calibrations of cyclopentanol using acetone solutions at eight different concentrations. 0.4 μL of each calibration solution were injected onto Tenax® cartridges, which were immediately desorbed under the same conditions as those resulting from the headspace sampling. The calibration was repeated three times and the data points averaged.

The following average headspace concentrations of cyclopentanol in ng/L air were measured:

| Time | Applied Voltage | | |
|---|---|---|---|
| [min] | 0 V | 60 V | 75 V |
| 10 | 38112 | 108509 | 128152 |
| 40 | 26618 | 71798 | 103436 |
| 70 | 22568 | 64060 | 73564 |
| 100 | 19076 | 52130 | 65369 |
| 130 | 17235 | 49236 | 59113 |
| 160 | 15006 | 44924 | 53621 |
| 190 | 13764 | 41618 | 48827 |
| 220 | 12566 | 38265 | 44759 |
| 250 | 12172 | 34217 | 41813 |
| 280 | 10806 | 32737 | 38292 |
| 310 | 10511 | 28819 | 34580 |
| 340 | 10200 | 28216 | 33646 |

After the headspace sampling, the ITO slides were each rinsed with about 500 μl of $CDCl_3$ (containing 1% of TMS). This solution (after the experiment) was analyzed by $^1H$ NMR spectroscopy and compared to 79.8 mg (80 μl) of the mixture of starting compounds (before the experiment). The following average values (three measurements) were obtained for the peak area ratio of the 4-butylaniline derivative (peak at 2.6 ppm) with respect to that of cyclopentanol (peak at 1.75 ppm):

| $^1H$ NMR peak ratio | 0 V | 60 V | 75 V |
|---|---|---|---|
| before experiment | 1:0.69 | 1:0.70 | 1:0.70 |
| after experiment | 1:0.41 | 1:0.33 | 1:0.22 |

The data show that the voltage applied to the cyclopentanol containing crystalline phase forming imine has an influence on the release of cyclopentanol. The release can thus be controlled by the strength of the electric field as illustrated in FIG. 3 (the higher the applied voltage, the faster the release).

Example 4

Headspace Analysis for the Release of a Mixture of Substances that can not Form New Imines by Constitutional Reorganization in the Presence of an Electric Field A series of flavor and fragrance alcohols, namely (−)-menthol (200.1 mg), (±)-linalool (199.1 mg) and (R)-citronellol (201.2 mg) as biologically active volatile compounds were mixed together and 20 μL of this mixture were added to 200 μL of N-(4-methoxybenzylidene)-4-butylaniline. Then 100 μL of the solution were placed between two ITO coated glass slides and the headspace concentrations of the three compounds were measured as described above (Example 3) by increasing the sampling time from 1 min to 2 min (and decreasing the purging time from 29 to 28 min). All experiments were carried out at least in triplicate at 75 V and 0 V (reference), respectively.

The following average headspace concentrations in ng/L air were measured:

| Time | Linalool | | Menthol | | Citronellol | |
|---|---|---|---|---|---|---|
| [min] | 0 V | 75 V | 0 V | 75 V | 0 V | 75 V |
| 10 | 4364 | 6580 | 2324 | 3108 | 1759 | 2079 |
| 40 | 2920 | 4584 | 1800 | 2536 | 1947 | 2442 |
| 70 | 2551 | 4016 | 1627 | 2302 | 2100 | 2763 |
| 100 | 2330 | 3712 | 1507 | 2112 | 2158 | 2850 |
| 130 | 2111 | 3664 | 1406 | 2104 | 2186 | 3006 |
| 160 | 1969 | 3348 | 1343 | 1940 | 2262 | 3109 |
| 190 | 1842 | 3155 | 1279 | 1823 | 2292 | 3104 |
| 220 | 1809 | 3025 | 1265 | 1742 | 2334 | 3044 |
| 250 | 1737 | 2919 | 1221 | 1664 | 2345 | 3075 |
| 280 | 1691 | 2944 | 1199 | 1682 | 2320 | 3102 |
| 310 | 1636 | 2871 | 1162 | 1638 | 2344 | 3099 |
| 340 | 1586 | 2940 | 1137 | 1692 | 2354 | 3263 |

Analysis of the $^1$H NMR data before and after the experiment (only performed once) confirmed the trend observed from the headspace measurements. The following values were obtained for the peak area ratio of the 4-butylaniline derivative (peak at 2.6 ppm, 2 H) to that of citronellol (peak at 3.6 ppm, 2 H), menthol (peak at 3.4 ppm, 1 H) and linalool (peak at 5.9 ppm, 1 H):

| molar ratio of 4-butyl-aniline:terpene alcohol | Citronellol | | Menthol | | Linalool | |
|---|---|---|---|---|---|---|
| | 0 V | 75 V | 0 V | 75 V | 0 V | 75 V |
| before experiment | 17.8:1 | 18.4:1 | 14.5:1 | 14.1:1 | 26.8:1 | 24.5:1 |
| after experiment | 18.1:1 | 21.8:1 | 14.8:1 | 16.3:1 | 28.2:1 | 32.9:1 |

The present measurements show that a voltage dependent release of fragrances is possible, even if fragrance mixtures are used. With the human olfactory thresholds of citronellol, menthol and linalool being at 46, 269 and 347 ng/L, respectively (see: Standardized Human Olfactory Thresholds, Eds.: M. Devos, F. Patte, J. Rouault, P. Laffort, L. J. van Gemert, Oxford University Press, Oxford, 1990), the measured headspace concentrations lie all far above this threshold value and the compounds can thus easily be smelled by humans for the entire duration of the experiment. The delivery system according to the invention thus allows to control the release of active substances depending on the strength of the applied electric field.

In a similar measurement, benzyl acetate (193.5 mg), (±)-4-octanolide (183.4 mg) and 2-methyldecanenitrile (215.8 mg) as biologically active volatile compounds were mixed together and 20 μL of this mixture were added to 200 μL of N-(4-methoxybenzylidene)-4-butylaniline. Then 100 μL of the solution were placed between two ITO coated glass slides and the headspace concentrations of the three compounds were measured as described above. All experiments were carried out at least in triplicate at 75 V and 0 V (reference), respectively.

The following average headspace concentrations in ng/L air were measured:

| Time | Benzyl Acetate | | 4-Octanolide | | 2-Methyl-decanenitrile | |
|---|---|---|---|---|---|---|
| [min] | 0 V | 75 V | 0 V | 75 V | 0 V | 75 V |
| 10 | 2321 | 3299 | 532 | 726 | 533 | 752 |
| 40 | 2329 | 3295 | 606 | 769 | 595 | 767 |
| 70 | 2191 | 3699 | 647 | 972 | 588 | 894 |
| 100 | 2093 | 3660 | 647 | 1032 | 579 | 908 |
| 130 | 2119 | 3589 | 692 | 1075 | 603 | 912 |
| 160 | 2072 | 3644 | 730 | 1120 | 623 | 939 |
| 190 | 2000 | 3724 | 737 | 1184 | 614 | 980 |
| 220 | 2056 | 3833 | 801 | 1235 | 656 | 1009 |
| 250 | 1986 | 3355 | 822 | 1066 | 665 | 860 |
| 280 | 1892 | 3744 | 817 | 1206 | 648 | 980 |
| 310 | 1787 | 3760 | 796 | 1266 | 628 | 1011 |
| 340 | 1615 | 3903 | 758 | 1333 | 595 | 1061 |

Analysis of the $^1$H NMR data before and after the experiment (only performed once) confirmed the trend observed from the headspace measurements. The following values were obtained for the peak area ratio of the 4-butylaniline derivative (peak at 3.8 ppm, 3 H) to that of benzyl acetate (peak at 5.1 ppm, 2 H) and 4-octanolide (peak at 4.4 ppm, 1 H). The peaks of 2-methyldecanenitrile overlapped with those of the 4-butylaniline derivative and were thus not integrated:

| molar ratio of 4-butylaniline: active compound | Benzyl Acetate | | 4-Octanolide | |
|---|---|---|---|---|
| | 0 V | 75 V | 0 V | 75 V |
| before experiment | 20.0:1 | 19.7:1 | 21.2:1 | 20.3:1 |
| after experiment | 21.3:1 | 23.1:1 | 21.2:1 | 22.8:1 |

The headspace concentrations measured in the presence of an electric field are higher than those measured in its absence, thus illustrating a controlled release effect of active molecules in dependence on the strength of the applied electric field.

Example 5

Headspace Analysis for the Release of a Mixture of Substances that can Form New Imines by Constitutional Reorganization in the Presence or Absence of an Electric Field A series of flavor and fragrance aldehydes and ketones, namely benzaldehyde (137.1 mg), 4-ethylbenzaldehyde (173.8 mg) and acetophenone (156.3 mg) as biologically active volatile compounds were mixed together and 20 μL of this mixture were added to 200 μL of N-(4-methoxybenzylidene)-4-butylaniline. Then 100 μL of the solution were placed between two ITO coated glass slides and the headspace concentrations of the three compounds together with that of 4-methoxybenzaldehyde (released from N-(4-methoxybenzylidene)-4-butylaniline) were measured as described above (Example 3). The experiments were carried out in duplicate at 75 V and 0 V (reference), respectively.

The following average headspace concentrations in ng/L air were measured:

| Time | Benzaldehyde | | Acetophenone | | 4-Ethyl-benzaldehyde | | 4-Methoxy-benzaldehyde | |
|---|---|---|---|---|---|---|---|---|
| [min] | 0 V | 75 V | 0 V | 75 V | 0 V | 75 V | 0 V | 75 V |
| 10 | 8940 | 22018 | 6782 | 11737 | 3167 | 4501 | 273 | 422 |
| 40 | 6148 | 14310 | 5659 | 11080 | 2483 | 4042 | 499 | 864 |
| 70 | 4338 | 10600 | 4961 | 10363 | 1847 | 3481 | 664 | 1250 |
| 100 | 3298 | 8373 | 4627 | 9684 | 1507 | 3012 | 802 | 1576 |
| 130 | 2542 | 7042 | 4320 | 9436 | 1241 | 2710 | 907 | 1867 |
| 160 | 1919 | 5935 | 3769 | 8811 | 968 | 2341 | 900 | 1980 |
| 190 | 1587 | 5000 | 3688 | 8542 | 878 | 2132 | 1024 | 2221 |
| 220 | 1289 | 4328 | 3444 | 8321 | 753 | 1963 | 1134 | 2370 |
| 250 | 1051 | 3757 | 3218 | 7851 | 656 | 1752 | 1186 | 2426 |
| 280 | 877 | 3202 | 3005 | 7426 | 568 | 1606 | 1180 | 2485 |
| 310 | 706 | 2873 | 2774 | 7299 | 493 | 1538 | 1181 | 2524 |
| 340 | 637 | 2463 | 2762 | 6681 | 461 | 1408 | 1215 | 2434 |

$^1$H and $^{13}$C NMR spectroscopy as well as GC/MS analysis combined with the comparison of GC retention times confirmed the formation of 4-methoxybenzaldehyde in the presence and absence of the electric field. Furthermore the generation of N-(4-ethylbenzylidene)-4-butylaniline and N-(benzylidene)-4-butylaniline was observed. The identity of the two butylaniline derivatives was verified by synthesis of the reference compounds and comparison of their spectroscopical data. N-(4-Ethylbenzylidene)-4-butylaniline and N-(benzylidene)-4-butylaniline were thus prepared by heating a mixture of 2.0 g of 4-butylaniline with 1 equivalent of the corresponding aldehyde in ethanol for about two days under reflux. Then more of the aldehyde was added and the reflux continued for a couple of hours. After cooling to room temperature, the solvent was removed and the crude product purified by bulb-to-bulb distillation (by removing the remaining excess of aldehyde) to give the two imines at quantitative yields. The products were characterized by $^1$H and $^{13}$C NMR spectroscopy and EI-mass spectrometry.

The present headspace measurements show that new imines are formed in the presence of active aldehydes or ketones. Although in this case the component exchange works in the presence and absence of the electric field, it was found that the amount of fragrance release is still dependent on the voltage applied. The headspace concentrations of aldehydes and ketones released in the presence of the electric field were in all cases higher than in the reference experiment where no electric field was applied as shown in FIG. 4. With the human olfactory thresholds of benzaldehyde and acetophenone being at 186 and 1820 ng/L, respectively (see: Standardized Human Olfactory Thresholds, Eds.: M. Devos, F. Patte, J. Rouault, P. Laffort, L. J. van Gemert, Oxford University Press, Oxford, 1990), the measured headspace concentrations lie far above this threshold value and the compounds can thus easily be smelled by humans for the entire duration of the experiment. Olfactory threshold data for 4-ethylbenzaldehyde and 4-methoxybenzaldehyde are not given in the cited reference.

In a similar experiment, 4-methoxybenzaldehyde (176.1 mg), acetophenone (159.3 mg) and benzaldehyde (137.6 mg) were mixed together and 20 µL of this mixture were added to 200 µL of N-(4-ethylbenzylidene)-4-butylaniline. Then 100 µL of the solution were placed between two ITO coated glass slides, and the film exposed to a voltage of 75 V or 0 V (reference), respectively, as described above. The measured headspace concentrations of 4-methoxybenzaldehyde, acetophenone and benzaldehyde were found to decrease continuously during the experiment, whereas an increasing amount of 4-ethylbenzaldehyde was measured with time. In the presence of the electric field (at 75 V) higher headspace concentrations were determined as compared to the reference sample (at 0 V).

The invention claimed is:

1. A method for releasing in a controlled manner, into the surrounding space, a $C_5$-$C_{30}$ volatile perfuming ingredient which method comprises the application of a variable electric field to a delivery system comprising:

1) at least one imine capable of forming a liquid crystalline phase and being of formula

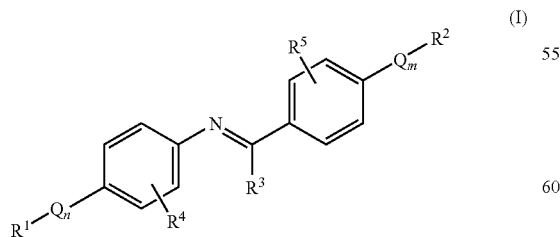

wherein $R^1$ and $R^2$ represent independently of each other a $C_1$-$C_{18}$ linear, branched or cyclic alkyl, alkenyl or alkoxy chain or a substituent selected from the group consisting of CN, OCOX, OCOC$_6$H$_5$X, C$_6$H$_5$X, COX, COOH, H, Cl, Br, I, NO$_2$, OH, CF$_3$, and N(CH$_3$)$_2$, wherein X is CF$_3$ or a $C_1$-$C_{18}$ linear or branched alkyl or alkenyl chain; and $R^3$ is H or a linear or branched $C_1$-$C_8$ alkyl or alkenyl chain;

n and m are 0 or 1, and with the proviso that n=m=1 is excluded; and

Q is selected from the group consisting of formulae i) to v),

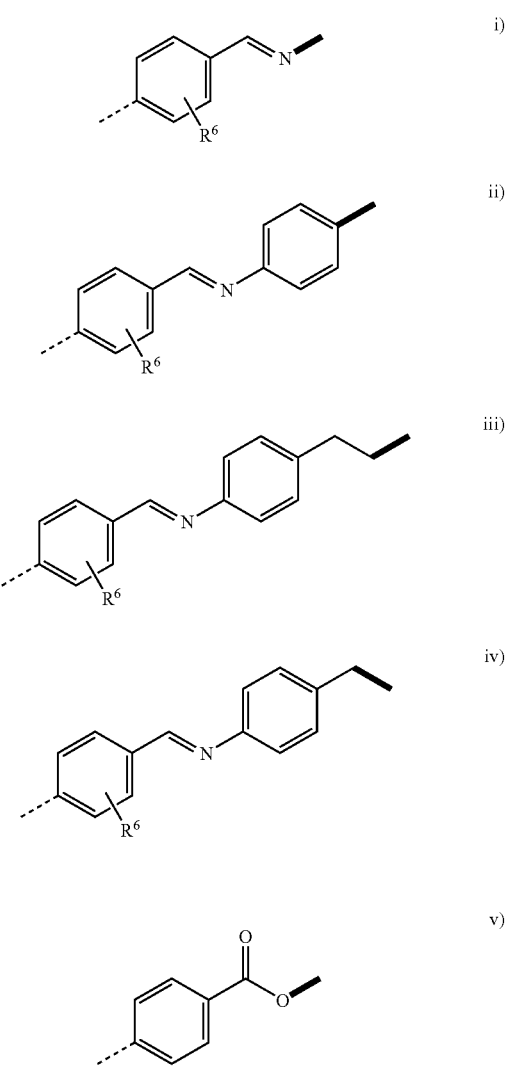

in which formulae if n=1 the dotted lines of formula i) to v) indicate the connection to R1 and the bold lines the connection to the aromatic ring of formula (I), if m=1 the dotted lines indicate the connection to the aromatic ring and the bold lines the connection to $R^2$; $R^4$, $R^5$ and $R^6$ are, independently from each other, selected from the group consisting of H, Cl, OH, OCH$_3$, CH$_3$, CN, NO$_2$, N(CH$_3$)$_2$; or $R^1$ and $R^4$, and/or $R^2$ and $R^5$, and/or $R^1$ and $R^6$, and/or $R^2$ and $R^6$ taken together, respectively, form a 5 or 6 membered ring containing 2 oxygen atoms; and with the proviso that at least one of the groups of $R^1$ or $R^2$ represents a $C_1$-$C_{18}$ linear or branched alkyl, alkenyl or alkoxy chain; and 2) at least one $C_5$-$C_{30}$ volatile perfuming ingredient.

2. The method of claim 1, wherein the compound of formula (I) is a compound of formula

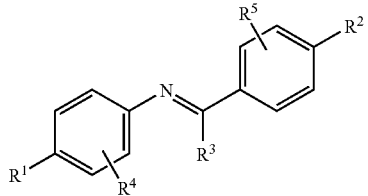

(II)

wherein $R^1$ and $R^2$ represent independently of each other a $C_1$-$C_{18}$ linear alkyl, alkenyl or alkoxy chain or a substituent selected from group consisting of CN, OCOX, OCOC$_6$H$_5$X, C$_6$H$_5$X, COX, COOH, and OH, wherein X is CH$_3$, CH$_2$CH$_3$, CH(CH$_3$)$_2$, or C(CH$_3$)$_3$;

$R^3$ is H or a linear or branched $C_1$-$C_4$ alkyl chain; and $R^4$ and $R^5$ are H, OH, OCH$_3$; or $R^1$ and $R^4$, and/or $R^2$ and $R^5$ taken together, respectively, may form a 5 or 6 member ring containing 2 oxygen atoms; and with the proviso that at least one of the groups of $R^1$ or $R^2$ represents a $C_1$-$C_{18}$ linear alkyl, alkenyl or alkoxy chain.

3. The method of claim 1, wherein the volatile perfuming ingredient is a compound having a molecular weight of between 80 and 250 g/mol and a vapor pressure above 0.05 Pa at standard conditions.

4. The method of claim 1, wherein the volatile perfuming ingredient is a $C_5$-$C_{15}$ volatile perfuming ingredient selected from the group consisting of alcohol, ester, ether, lactone, nitrile, aldehyde, ketone, and a mixture thereof.

5. The method of claim 1 wherein the compound (I) of the delivery system is obtained by condensation of amines (IV) with carbonyl derivatives (III)

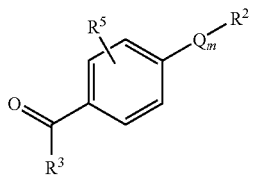

(III)

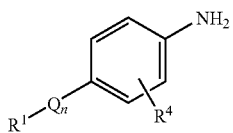

(IV)

wherein $R^1$, $R^2$, $R^3$, $R^4$, $R^5$, Q, n and m have the same meaning as in claim 14; and the compounds (III) and (IV) have a volatility lower than those of the biologically active volatile aldehyde, ketone or amine.

6. The method of claim 1, wherein $R^3$ is H.

7. The method of claim 1, wherein the delivery system comprises a compound of formula (I) and at least one $C_5$-$C_{15}$ volatile perfuming ingredient, the ingredient being an alcohol, ester, ether, lactone, or nitrile.

8. The method of claim 1 wherein the delivery system further comprises an apparatus allowing the application of an electric field to the delivery system, with the apparatus being in contact with the delivery system.

9. The method of claim 1 wherein the delivery system further comprises means to apply an electric field, or a voltage, connected to the apparatus.

10. The method of claim 1, wherein the delivery system is in the form of a film and further comprises an apparatus allowing the application of an electric field to the delivery system, with the apparatus being in contact with the delivery system and including two conducting surfaces to which a constant or variable electric field can be applied, and between which is inserted the film, and which are in contact with the film.

11. The method of claim 10, wherein the delivery system further comprises means to apply an electric field, or a voltage, connected to the apparatus.

12. The method of claim 1, wherein the delivery system is contained within or is associated with a consumer article.

13. The method of claim 12, wherein the consumer article is in the form of an air freshener, a car freshener, a closet freshener, a cat litter box freshener, a shoe freshener or a garbage pail freshener.

14. The method of claim 2, wherein $R^3$, $R^4$ and $R^5$ are a hydrogen atom, $R^2$ is methoxy and $R^1$ is butyl such that the compound of formula II is N-(4-methoxybenzylidene)-4-butylaniline.

* * * * *

UNITED STATES PATENT AND TRADEMARK OFFICE
CERTIFICATE OF CORRECTION

PATENT NO. : 8,158,135 B2
APPLICATION NO. : 12/294398
DATED : April 17, 2012
INVENTOR(S) : Lehn et al.

It is certified that error appears in the above-identified patent and that said Letters Patent is hereby corrected as shown below:

Title Page:
Item (56) References Cited, FOREIGN PATENT DOCUMENTS:
  After "EP 576 551 B1" change "5/1995" to -- 1/1994 --.
Item (56) References Cited, OTHER PUBLICATIONS:
  "C.C. Müller-Goyman" reference, change "Müller-Goyman" to -- Müller-Goymann --.
Item (57) ABSTRACT:
  Line 3, after "at least", delete "with".

Column 5:
Line 26, change "$(T_{IN})$" to -- $(T_{I/N})$ --.
Line 31, change "methoxybenzylidene)-4-butylaniline" to -- ethoxybenzylidene)-4-butylaniline --.

Column 20:
Line 10, change "claim 14;" to -- claim 1; --.

Signed and Sealed this
Twenty-ninth Day of May, 2012

David J. Kappos
*Director of the United States Patent and Trademark Office*